(12) United States Patent
Gogoussis et al.

(10) Patent No.: US 11,166,738 B2
(45) Date of Patent: Nov. 9, 2021

(54) WRAPPING CAPE SYSTEM FOR RETRIEVAL OF BLOCKING ITEMS IN TUBULAR ENVIRONMENTS

(71) Applicants: Aristides Gogoussis, Pylaia Thessalonikis (GR); Stefanos Finitsis, Kalamaria Thessalonikis (GR)

(72) Inventors: Aristides Gogoussis, Pylaia Thessalonikis (GR); Stefanos Finitsis, Kalamaria Thessalonikis (GR)

(73) Assignees: Stefanos Finitsis, Kalamaria (GR); Aristides Gogoussis, Pylaia (GR)

( * ) Notice: Subject to any disclaimer, the term of this patent is extended or adjusted under 35 U.S.C. 154(b) by 157 days.

(21) Appl. No.: 16/494,024

(22) PCT Filed: Mar. 13, 2017

(86) PCT No.: PCT/GR2017/000011
§ 371 (c)(1),
(2) Date: Sep. 13, 2019

(87) PCT Pub. No.: WO2018/167521
PCT Pub. Date: Sep. 20, 2018

(65) Prior Publication Data
US 2020/0085454 A1    Mar. 19, 2020

(51) Int. Cl.
*A61B 17/221* (2006.01)
*A61B 17/00* (2006.01)

(52) U.S. Cl.
CPC .. *A61B 17/221* (2013.01); *A61B 2017/00292* (2013.01); *A61B 2017/00867* (2013.01); *A61B 2017/2212* (2013.01)

(58) Field of Classification Search
CPC .......... A61B 17/221; A61B 2017/2212; A61B 2017/2217; A61B 2017/2215
See application file for complete search history.

(56) References Cited

U.S. PATENT DOCUMENTS

| | | | | |
|---|---|---|---|---|
| 5,192,286 A * | 3/1993 | Phan | ...................... | A61B 17/02 604/264 |
| 6,936,059 B2 * | 8/2005 | Belef | ...................... | A61F 2/013 606/200 |

(Continued)

FOREIGN PATENT DOCUMENTS

| EP | 2486875 A2 | 8/2012 |
|---|---|---|
| JP | H06509259 A | 10/1994 |

(Continued)

OTHER PUBLICATIONS

International Search Report for PCT/GR2017/000011 dated Nov. 15, 2017, 4 pages.

*Primary Examiner* — Tuan V Nguyen
(74) *Attorney, Agent, or Firm* — Warner Norcross + Judd LLP

(57) ABSTRACT

Disclosed is a wrapping cape system which displays favorable grasping characteristics in operations for the entrapment and removal of blocking items in tubular geometries. The wrapping cape system yields a configuration that surrounds the blocking item, such as a thrombus, peripherally, thus capturing its body tangentially and allowing the operator to pull it along the surrounding tube (for instance vein or artery) by utilizing shear forces distributed along the surface of the blocking item in its axial direction. The advantage stems from the fact that the blocking item is not pushed from behind during its withdrawal, but pulled instead; also, since there is no penetration, fragmentation is avoided.

12 Claims, 9 Drawing Sheets

(56) References Cited

U.S. PATENT DOCUMENTS

| | | | |
|---|---|---|---|
| 7,094,249 B1 | 8/2006 | Broome et al. | |
| 2002/0026203 A1 | 2/2002 | Bates et al. | |
| 2002/0095171 A1* | 7/2002 | Belef | A61F 2/013 606/200 |
| 2003/0135223 A1* | 7/2003 | Teague | A61B 17/221 606/127 |
| 2007/0288054 A1 | 12/2007 | Tanaka et al. | |
| 2013/0006284 A1 | 1/2013 | Aggerholm et al. | |
| 2013/0184739 A1 | 7/2013 | Brady et al. | |
| 2013/0317515 A1 | 11/2013 | Kuroda et al. | |
| 2018/0132873 A1* | 5/2018 | Sirivong | A61B 17/221 |

FOREIGN PATENT DOCUMENTS

| | | |
|---|---|---|
| JP | H06509259 A | 10/1994 |
| JP | 2008068064 A | 3/2008 |
| JP | 2008068064 A | 3/2008 |
| JP | 2008100078 A | 5/2008 |
| JP | 2008100078 A | 5/2008 |
| WO | 199302732 A1 | 2/1993 |
| WO | 2011135556 A1 | 11/2011 |
| WO | 2013018445 A1 | 2/2013 |
| WO | WO2013/018445 A1 | 2/2013 |

\* cited by examiner

FIG. 9A                    FIG. 9B

WRAPPING CAPE SYSTEM FOR RETRIEVAL OF BLOCKING ITEMS IN TUBULAR ENVIRONMENTS

CROSS-REFERENCE TO RELATED APPLICATIONS

This application is the National Stage of International Application No. PCT/GR2017/000011 filed on 13 Mar. 2017, the contents of which are hereby incorporated by reference.

The invention is referred to a wrapping system which displays favorable grasping characteristics in operations requiring the entrapment and removal of blocking items in tubular geometries.

There are a number of situations where an item is caught at a narrower cross-section of a tubular guide; when the scale is small so that direct human intervention is not possible, the need arises to approach the blocking item indirectly and somehow trap it in order to remove it. A major domain where such capabilities are valuable is the medical field. Examples of blocking items are clots, kidney stones, stones in general, bodily materials as well as foreign bodies. What is needed in such cases is a safe way of approaching the item to be removed and an entrapment system to capture and remove the blocking item without breaking it into smaller pieces and without damaging the surrounding tissues. For instance, thromboembolic diseases such as myocardial infarction, pulmonary embolism, peripheral thrombosis, organ embolism, etc. are typically triggered by a thromboembolus (hereinafter briefly referred to as thrombus), i.e. a viscoelastic blood clot composed of blood platelets, fibrinogen, clotting factors, etc., which has become stuck in a blood vessel and occludes it entirely or partly. An occlusion of organ arteries leads to an interruption in the supply of the dependent tissue with oxygen and nutrients. The disturbance of the functional metabolism accompanied by a loss of function is followed by a failure of the structural metabolism within a short period of time, entailing a destruction of the affected tissue (infarct). The most common organs affected thereby with human beings are the heart and the brain. But such changes also affect limb arteries and pulmonary arteries. Venous thrombosis and thromboembolic occlusion frequently appear in leg and pelvic veins, pulmonary veins and other veins of the body, and may cause significant short-term and long-term morbidity and mortality, renal and biliary stones or other items in bodily cavities. The pathology of thrombotic occlusion of an intracranial sinus may cause severe intracerebral hemorrhage due to a disturbance in the venous drainage of the brain tissue.

In view of the severity of disease patterns triggered by thromboembolism and considering the frequency of these diseases, there are various techniques known from prior art and developed for dissolving or removal of thrombi. For example, patients are treated with thrombolytic means such as streptokinase, urikinase, alteplase or with anticoagulants serving for thrombolysis or containment of thrombus growth. As these treatment methods in most cases are time-consuming, they are often combined with methods serving for medical diminution or removal of the thrombus and embolus, respectively.

Apart from open surgical interventions, transluminal and/or endovascular catheter-guided interventional therapy methods are increasingly applied in state-of-the-art technology because these methods are less invasive. Such methods aim to remove a thrombus by means of suction catheters generating a negative pressure, or mechanically by means of catheters equipped with capturing cages, helixes, hooks, stent-like structures or stentrievers or the like, from a patient's body.

A drawback of thrombolytic treatment methods lies in that they are rarely successful once the available time frame has elapsed. But even the transluminal/endovascular devices frequently are unable to remove a thrombus completely, there also being a risk in that the thrombus or fragments thereof are released and entrained as freight in the blood stream to smaller vessels where they are harder to reach and treat. In general, prior art devices frequently either cause wedging of the blocking items with the wall of the surrounding tissues, or lead to partial or total fragmentation of the occluding item, or, owing to their dimensions and/or low flexibility, they are insufficiently able to remove smaller-vessel thrombi, especially like those in the brain.

What would be helpful for overcoming the limitations of prior art devices is a wrapping design. A netted wire based wrapping action yields a configuration that surrounds the blocking item, such as a thrombus, peripherally thus capturing its body tangentially and allowing the operator to pull it along the surrounding tube (for instance vein or artery) by utilizing shear forces distributed along the surface of the blocking item in its axial direction. The advantage stems from the fact that the blocking item is not pushed from behind during its withdrawal. For example, when a clot is pushed it tends to wedge onto the walls of the vessel and the total resisting friction increases, as in self-locking situations. So, if the clot is not pushed but pulled instead, those undesirable conditions are avoided. Moreover, when the drawing forces are distributed over an extended area, and furthermore when the clot is squeezed peripherally, it is less prone to wedging, since it tends to get rather slimmer; as a result, it becomes less subject to friction and less likely to subdivide into more pieces, since it is enveloped uniformly.

The aims of a favorable such design can be primarily achieved by deploying a slim tubular guide, (from now on called a catheter), through which either two or more netted wires suitably pre-arranged pass through, and once brought into contact with the blocking item (which could be a thrombus or clot), they act in a coordinated wrapping fashion in order to grasp it. This is achieved mechanically, given that the wires are inter-assembled in a way that once the catheter has been guided to the targeted location (flush with the blocking item) and after it is partially withdrawn, subsequently, to permit the furnishing of the joint action of the wires and the interconnecting net, the overall geometry forces the mutual interaction of the assembly with that of the blocking item, and with the walls of the surrounding tube (which could be a vessel), to conform to the surrounding geometry. When the blocking item has been thus grasped, the whole compound arrangement consisting of the catheter, the wires, the net, and the blocking item, is pulled and ultimately removed from the vessel.

In accordance with the invention the core of the basic design consists of a system comprising a catheter, a spinal wire and a chordal wire aligned with it, equipped with a web-like contractible-expandable net and a pulling string, where on deployment of the system it transforms into a conical or conical-and-cylindrical wrapper that envelops and tightens the blocking item allowing for its subsequent removal. The spinal wire is stiffer than the chordal wire. One end of the chordal wire is attached to the end-point of the spinal wire. The wire assembly is passed through the catheter and brought to the distal end of it. The catheter is guided to the location of the blocking item. Then the wire assembly is driven through the catheter all the way to the catheter's outlet. Following that, the catheter is partially withdrawn by some distance, d, (approximately proportional to the length of the blocking item, yet somewhat longer), but the wires are not pulled along, instead they are held in their original place. Consequently, both wires are revealed and are exposed necessarily by the same distance, d, each. Next, a relative sliding motion is implemented between the spinal and chordal wires, in a way that beyond the distal end of the catheter the exposed lengths of the spinal wire and the chordal wire are modified with respect to their original length, ultimately resulting in unequal lengths whereby the ratio of {(chordal length)/(spinal length)} is greater than one. Such an outcome may be achieved in a number of ways such as by a coordinated pulling and pushing of the spinal and chordal wires, respectively, or by pulling the spinal wire while maintaining the length of the chordal wire, or, vise-versa, by keeping the length of the spinal wire invariant while lengthening the chordal wire. In any case, as a result of this antagonistic action and in conjunction with a conforming expandable net, the chordal wire is reconfigured into a loop-like shape since its exposed length is longer than that of the spinal wire, and because it is more flexible than the stiffer spinal wire. Given that the shape of the surrounding geometry (e.g. a blood vessel) is cylindrical and, likewise, the shape of the blocking item obstructing it resembles that of an elongated cylindrical ellipsoid, the chordal wire is forced to comply with the cylindrical geometry and assume a bi-partite helicoidal shape, with two opposite—in sense— spiral branches originating from the middle of the chordal wire toward its two ends. The resulting shape therefore embraces the blocking item with the aid of the web-like contractible and expandable net, which links the chordal wire and the spinal wire while simultaneously it is constrained by them, having them as its boundaries. So, the blocking item is captured peripherally once the wrapping motion is enacted. Next, the chordal wire is pulled via a string attached near or at the middle of its exposed length, forcing the net to assume a conical shape, which surrounds the blocking item entirely from its distal side thus securing its impending withdrawal. Subsequently, the chordal wire is pulled individually, causing the net to implement extra tightening to the blocking item. At this stage the whole assembly comprising the catheter, the wires, the string, the net, and the captured blocking item, may be withdrawn away thus de-clogging the occluded tube.

In addition to the main twin-wire configuration which was just described, it is possible to implement a triple-wire configuration or even a multi-wire configuration. Examples of a triple wire configuration may be: a spinal wire with two equal chordal wires or a spinal wire with two unequal wires. In the first variety, the two chordal wires may surround the blocking item either from the same side or from opposite sides (in a double-arm hug configuration). In the second variety, whereby two chordal wires of unequal lengths are deployed, they are connected to each other near or at their exposed middle (exposed in the sense that the guiding tube, such as a catheter, has been withdrawn thus exposing these wires) and they are linked to each other by a net consisting of fibers forming a lattice of conforming rhomboid or parallelogram patterns. A generalization to multiple-wire configurations is possible, in association with suitable enveloping types of the accompanying net patterns, as will be discussed in more detail later.

In all options of wire configurations, it is possible to obtain an optimal initial orientation of the assembly with respect to the blocking item if a precursory guiding wrapping loop is utilized. The guiding wrapping loop constitutes a physical extension of the distal end of the basic configuration. The principle of operation is exactly the same as that of the twin-wire configuration. There is an additional feature whereby the chordal wire is equipped with an eyelet through which the spinal wire passes through. When the spinal wire is pulled, a point is reached where relative displacement of the spinal and chordal wires is no longer possible due to a slight bulge at the thickness of the spinal wire. The procedure consists of two phases. During the first phase the catheter is brought sufficiently beyond the blocking item so that when partially withdrawn it reveals the guiding wrapping loop, which necessarily finds itself also beyond the blocking item. The spinal cord is pulled and the wrapping action settles unimpededly the chordal wire of the guiding wrapping loop around the internal wall of the surrounding tube. This way the spinal and chordal wires are aligned with the confining wall and consequently they also prepare the proper orientation for the preceding portion of the main twin or triple-wire assembly. The second phase consists in following the standard procedure which coordinates the wires for wrapping the blocking item in the manner explicitly described earlier.

In all the aforementioned design configurations two main enveloping types involving the pattern of the accompanying net are deployed, depending on the geometry determined by the spinal and chordal wires. The term "wrapping cape" refers to any of the enveloping types described below. In both types of enveloping the spinal cord and a chordal wire are connected by a web-like net of uniform or non-uniform pattern whose geometry has to comply with the contraction condition that when the spinal wire and the chordal wire are aligned, the net is contracted in one dimension and elongated in the other, thus co-aligned with the spinal and chordal wires. When the spinal and chordal wires are in a state of separation the net is expanded and undertaking a two-dimensional shape.

In the first type of enveloping, which may be called the triangular type, the contraction condition is met when the fibers of the net are interwoven suitably, such as when they form, for instance, combinations of appropriate parallelogram or rhomboid patterns, with sides slanted with respect to the spinal wire and parallel to the sides of the chordal wire. One end of each such fiber of the net is fixed at some point belonging to the posterior side of the chordal wire and the other end is fixed at some point of the distal side of the chordal wire; the fiber itself is going once around the spinal wire, and its total length equals the length of the segment of the chordal wire that is defined by the two points where the fiber is fixed. All the fibers together, in the expanded state, are confined by a triangularly shaped outline formed by the spinal and chordal wires. The spinal wire may be considered the base of this triangle while the chordal wire represents the other two sides of it. The triangle need not be equilateral.

Also, a shape-curving generalization is possible, whereby the sides of the triangle are curvilinear, thus resembling a circular arc; in addition, the cells of the net need not be only quadrilaterals but they can be polygonal as well. The only condition required is that the contraction condition be imposed on the pattern of the net. More specifically, for each cell the lengths of its edges should satisfy an equality condition: in the collapsed state, in which the cell edges are collinear, the cell (a) aligns with both the spinal and the chordal wires, and (b) degenerates into a straight-line segment having as its ends two of the polygon's vertices, the sum of the lengths of the consecutive edges of the two branches of the polygon that end up forming the collapsed line segment, should be equal to each other. For instance, if a cell is pentagonal and has edges with lengths a, b, c, d, e, then a+b=c+d+e, assuming that the corresponding edges form the two branches that yield the closed configuration.

The second type of enveloping, which may be called the trapezoidal type, has many versions, out of which three types will be described. The first type involves the deployment of two chordal wires of unequal lengths and it corresponds to the second variety of the triple-wire configurations described earlier. The shorter chordal wire is connected with the longer chordal wire near or at the middle of the exposed length of the longer chordal wire. The distal end of the shorter wire is connected to the spinal wire while the proximal end is connected to the chordal wire. The shorter chordal wire is linked to the spinal wire with a subnet having a triangular outline, when expanded, with a pattern in accordance with the first option, and to the longer chordal wire with two separate surrounding subnets consisting of fibers forming a lattice of conforming parallelogram patterns having one side parallel to the spinal wire and the other side parallel to the adjacent side of the triangle formed by the shorter chordal wire. Thus, the total external profile, which is determined by the longer chordal wire, is trapezoidal during expansion. The second type may be considered a special case of the first type whereby the shorter wire is replaced by a fiber. This way the originally distinct subnets, when expanded, are unified into one single net consisting or two individual patterns: one pattern with a triangular outline at the core, and two patterns with parallelogram outline, each, bordering the triangular core. As in the first case, the parallelogram-outline patterns bordering the triangular outline core of the net may be unequal in size whilst the wired profile remains trapezoidal (the spinal wire forming the base of the trapezium). For instance, the proximal parallelogram might be five times as long as the distal one or the distal parallelogram might have zero size and therefore it may be omitted altogether. The third type may be considered a generalization of the second version whereby any individual fiber, or any combination of connected segments of fibers, may be replaced by one or more wires.

In the trapezoidal type of enveloping the pulling string is attached to the proximal vertex of the shorter base of the trapezoidal profile.

The chordal wires in all cases may be uniformly softer than the spinal ones or gradually softer along their length, reaching local maxima of softness or hardness at certain locations, so they curve in accordance with the intended geometry. The required flexibility for the chordal wires, or for certain portions of them when localized bending is required, may be achieved either by employing the same material but varying-area cross-sections, or by using materials of varying softness length-wise. In some cases, it is preferable not to reduce the thickness of the chordal wires when trying to achieve the desirable softness. It might even be necessary to increase the width of the chordal wires without increasing their stiffness. Although seemingly impossible, this peculiar specification can be satisfied. The solution is to use spirally wound designs at places or all over. An additional enhancement toward facilitating the handling of the chordal wires during operation may be accomplished if they are bended in advance at proper articulations so that they are predisposed with an innate tendency to seek their final shape.

As for other details of the present invention, materials and manufacturing techniques may be employed as within the level of those with skill in the relevant art. The same may hold true with respect to method-based aspects of the invention in terms of additional acts that are commonly or logically employed. In addition, though the invention has been described in reference to several examples, optionally incorporating various features, the invention is not to be limited to that which is described or indicated as contemplated with respect to each variation of the invention.

Various changes may be made to the invention described and equivalents (whether recited herein or not included for the sake of some brevity) may be substituted without departing from the true spirit and scope of the invention. Also, any optional feature of the inventive variations may be set forth and claimed independently, or in combination with any one or more of the features described herein. Accordingly, the invention contemplates combinations of various aspects of the embodiments or combinations of the embodiments themselves, where possible. Reference to a singular item, includes the possibility that there are plural of the same items present.

The singular forms "a," "and," "said," and "the" include plural references unless the context clearly dictates otherwise. It is important to note that where possible, aspects of the various described embodiments, or the embodiments themselves can be combined where such combinations are intended to be within the scope of this disclosure.

The invention is described below with reference to indicative figures depicting a thrombectomy operation.

FIGS. 9A, 9B and 9C depict three variations of the net pattern of the trapezoidal profile configuration.

Figure 1A:
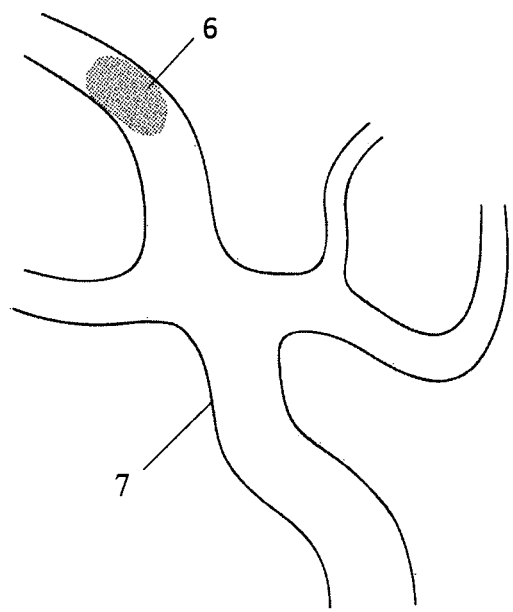
FIG. 1A depicts a thrombus blocking a vessel.

In FIG. 1A a thrombus, (6), is blocking the flow of blood through vessel (7).

Figure 1B:
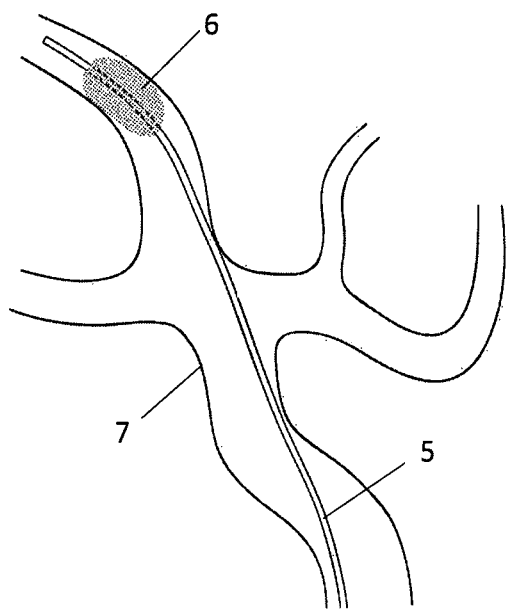
FIG. 1B depicts a catheter positioned flush with the thrombus.

In FIG. 1B the catheter, (5), is brought to the location of the thrombus (6), and is positioned past it.

Figure 1C:
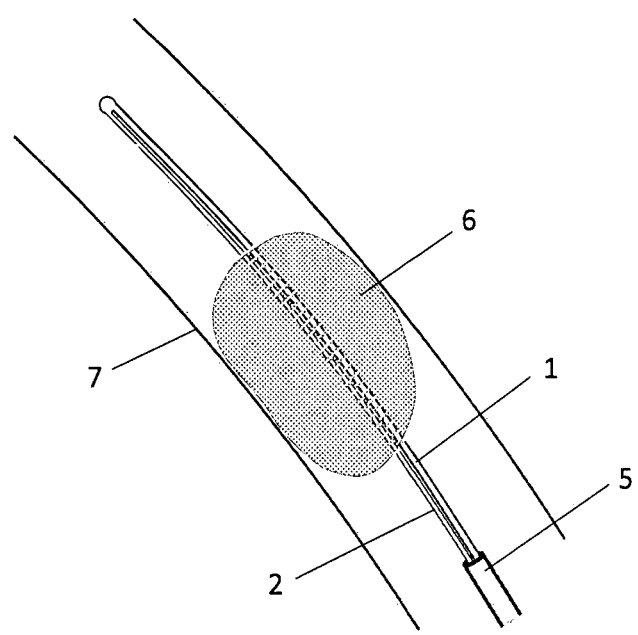
FIG. 1C depicts a magnified view of the spinal and chordal wires after the catheter is withdrawn partially.

In FIG. 1C the catheter, (5), is withdrawn partially and thus the spinal wire (1) and chordal wire (2) are revealed.

Figure 2A:
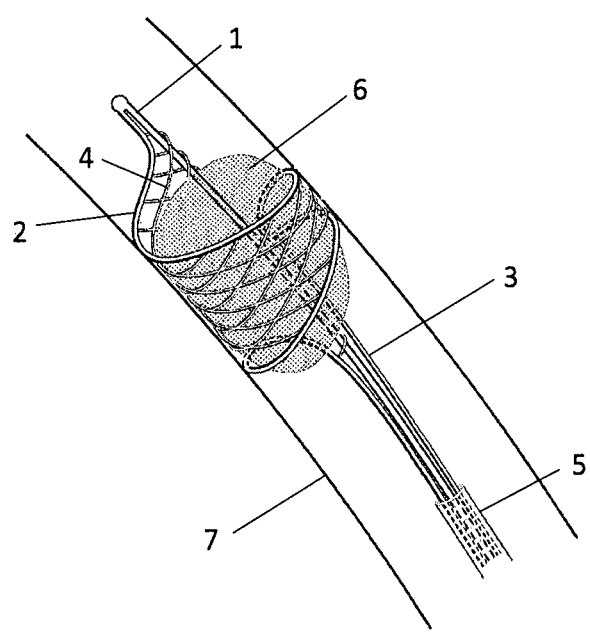
FIG. 2A depicts the wrapping of the thrombus by the chordal wire and the net.

In FIG. 2A the spinal wire (1) is pulled with respect to the chordal wire (2) and the chordal wire along with the accompanying net, (4), encircle the thrombus, (6); the string (3) is straightened.

Figure 2B:
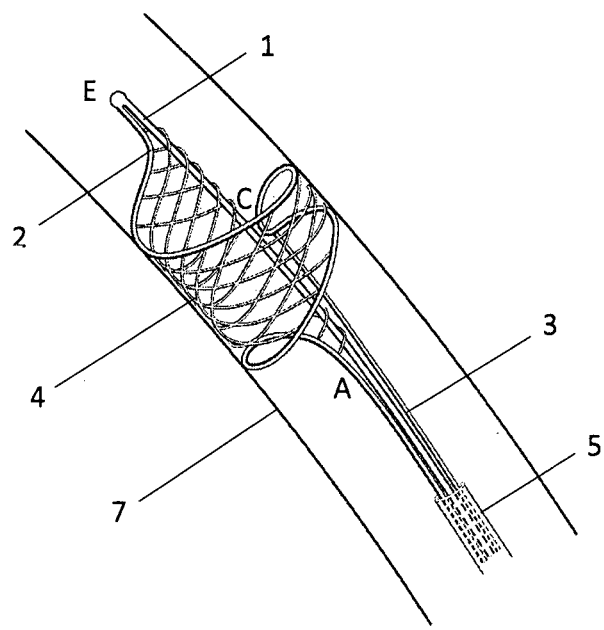
FIG. 2B depicts the wrapping configuration alone without the thrombus.

In FIG. 2B the wrapping configuration which is obtained after the spinal wire (1) is pulled with respect to the chordal wire (2) is shown without a thrombus inside the net, (4). The distal part of the chordal wire, EC, and the proximal part of the chordal wire, AC, are of helicoidal shape but they are opposite in spiraling sense.

Figure 2C:
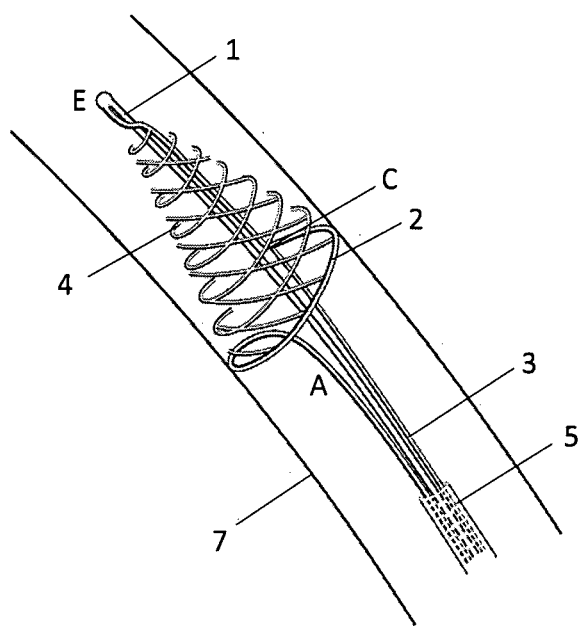
FIG. 2C depicts the reshaping of the wrapping setup into a conical configuration.

In FIG. 2C the string (3), which is attached at point C of the chordal wire (2), is pulled, causing alignment of the distal portion EC of the chordal wire (2) with the spinal wire (1), thus imposing a conical shape to the wrapping net, (4).

Figure 2D:
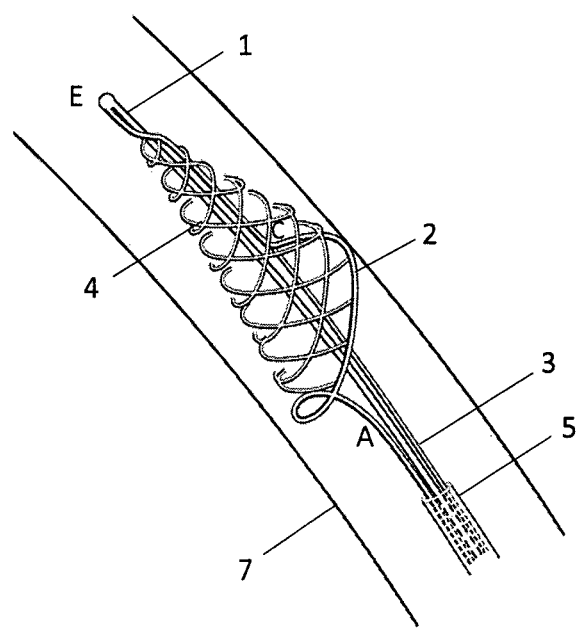
FIG. 2D depicts the tightening of the conical configuration.

In FIG. 2D, after the conical shape is obtained following the initial wrapping due to the pulling of string (3), the chordal wire (2) is pulled while the spinal wire (1) and the string (3) are held together; this results in narrowing of the conical shape of the net, (4).

Figure 2E:
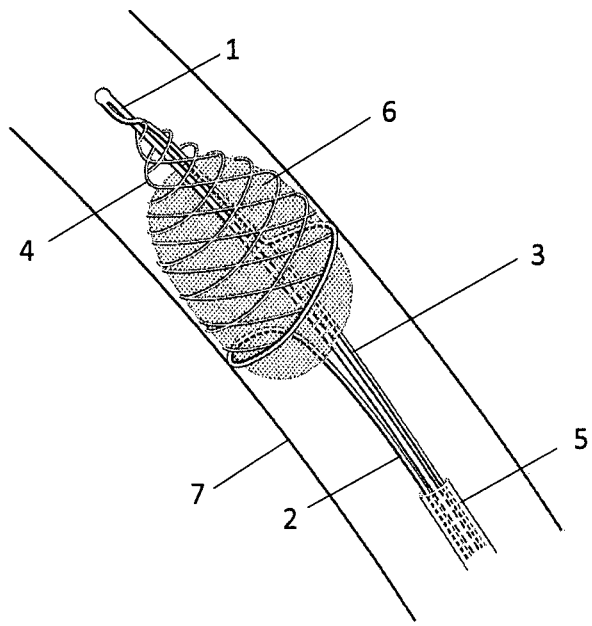
FIG. 2E depicts the reshaping of the wrapping setup into a conical configuration surrounding the thrombus.

In FIG. 2E the thrombus, (6), is shown captured inside the conical shape of the net, (4), formed after encirclement of the thrombus by the chordal wire (2) and pulling of the string (3).

Figure 2F:
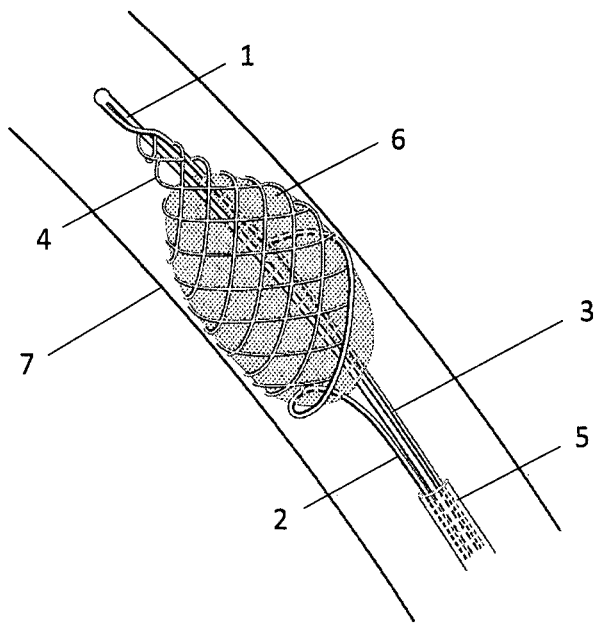
FIG. 2F depicts the tightening of the conical configuration incorporating the thrombus.

In FIG. 2F it is shown how the narrowing of the conical shape of the net, (4), formed by pulling the chordal wire (2) while the spinal wire (1) and the string (3) are held together, causes extra tightening of the thrombus, (6), by the net, (4); the whole assembly may be removed, de-clogging the vessel.

Figures 3A, 3B, 3C:
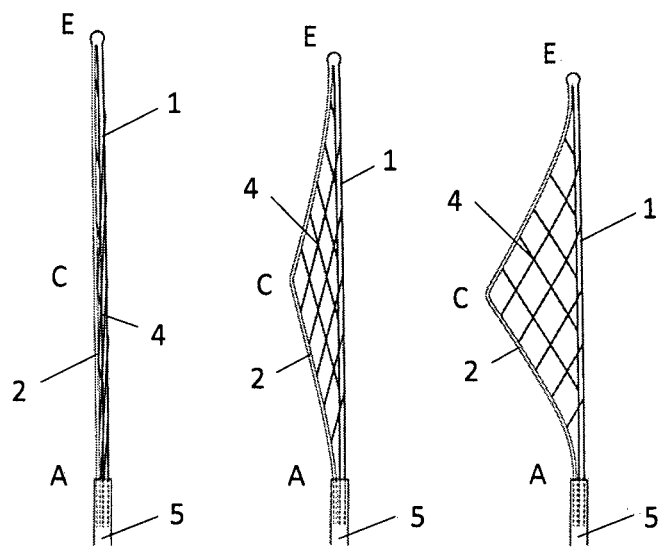
FIGS. 3A, 3B, 3C depict three phases of the triangular profile configuration comprising the chordal wire, the spinal wire, and the net: fully closed, semi-open, and fully open development, respectively.

In FIG. 3A the triangular profile configuration is illustrated in its initial state before expansion of the chordal wire (2) and development of the net, (4). Letters A, C, and E, represent the proximal, middle, and distal points of the chordal wire, respectively; in general, point C which belongs to the chordal wire and to which string (3) is permanently attached, may be an intermediate point of AE.

In FIG. 3B the triangular profile configuration is depicted in a semi-expanded unwrapped transitory state. The fibers of the net (4), have their ends fixed at the chordal wire (2) after going once around the spinal wire (1), and are pre-arranged so that they form parallelogram cells with sides parallel to the sides of the chordal wire (2) in its deformed state. The net is contractible and thus collapses, practically, to a minimal structure when the chordal wire is inside the catheter, or outside the catheter in the closed configuration just before deployment of the expansive step; wires (1) and (2) are linked to each other via net (4), in a way such that if A is a specific point of the chordal wire (2), then any fiber attached to some intermediate point H of AC and to a point H' of CE, after going once around the spinal wire (1) at some point C', satisfies the compatibility condition that HC'=CH' and C'H'=AC, which also implies that the length of the fiber, $l_f$, equals the length of HH' of the chordal wire (2).

Also, the net contracts whenever the chordal wire (2) is pulled for extra tightening of the thrombus during the phase of narrowing the capturing cone.

In FIG. 3C the triangular profile configuration is shown in fully expanded unwrapped development.

Figure 3D:
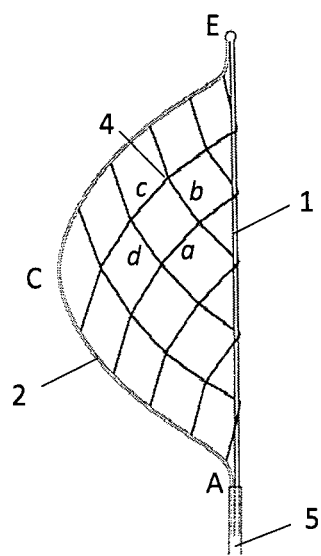
FIG. 3D depicts a curved triangular profile in expansion and states the contraction condition for any cell of the net.

In FIG. 3D a curved triangular profile in expansion is shown where the cells of the net are quadrilaterals. The compatibility condition which guarantees that the net (4) is contractible and thus collapses, practically, to a minimal structure, also holds for the curvilinear case. In this case the contraction condition applied to any cell of the net, such as the one depicted herein, is a+b=c+d, where a, b, c, and d, are the lengths of the edges of the respective quadrilateral.

Figure 4:
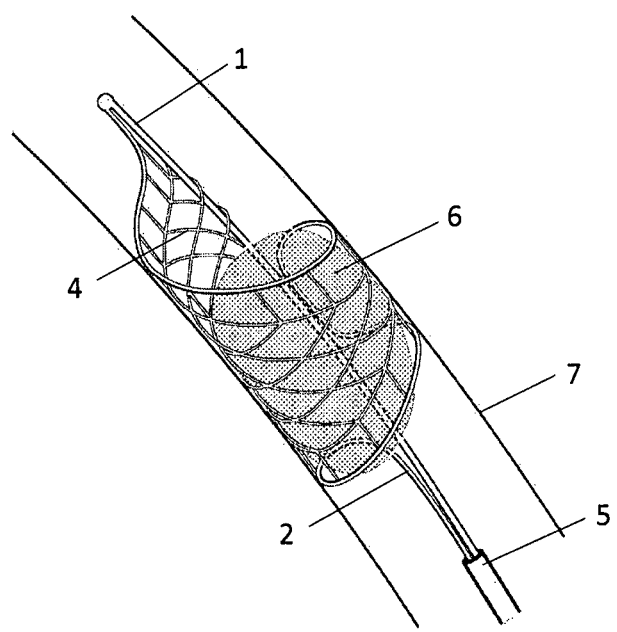
FIG. 4 depicts the wrapping of the thrombus by the chordal wire and the net in a trapezoidal-type setup.

In FIG. 4 the wrapping of the thrombus, (6), by the chordal wire (2) and the net, (4), in a trapezoidal-type setup is shown.

Figures 5, 6:
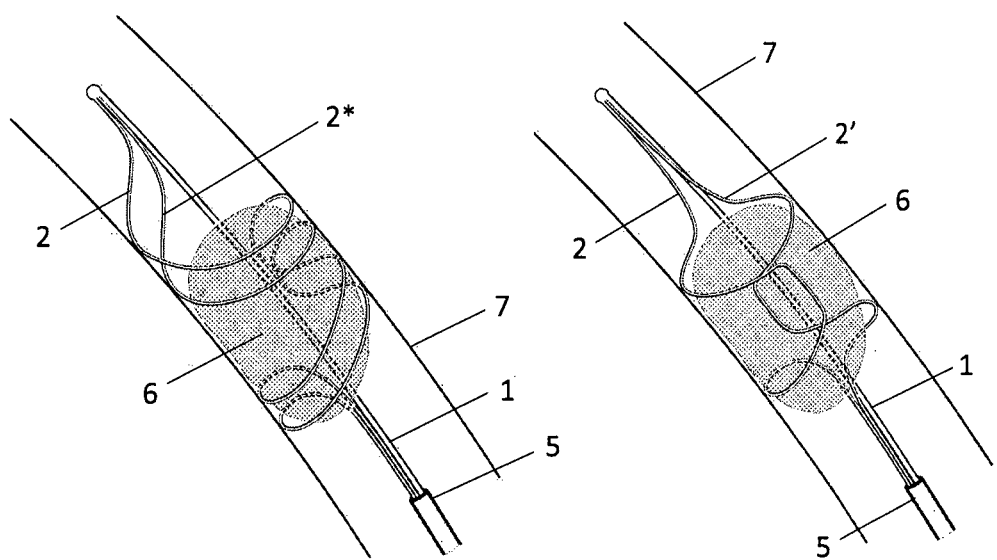
FIG. 5 depicts the wrapping of the thrombus by a compound chordal arrangement consisting of two wires: a longer one (external) and a shorter one (internal).
FIG. 6 depicts the wrapping of the thrombus by two embracing chordal wires.

In FIG. 5 the wrapping of the thrombus, (6), by a compound chordal arrangement consisting of two wires, a longer one (external), (2), and a shorter one (internal), (2*), is shown without any accompanying net, to illustrate the underlying geometry.

In FIG. 6 the wrapping of the thrombus, (6), by two embracing chordal wires (2) and (2') in a transitory state is shown without any accompanying net, to illustrate the underlying geometry.

Figure 7:
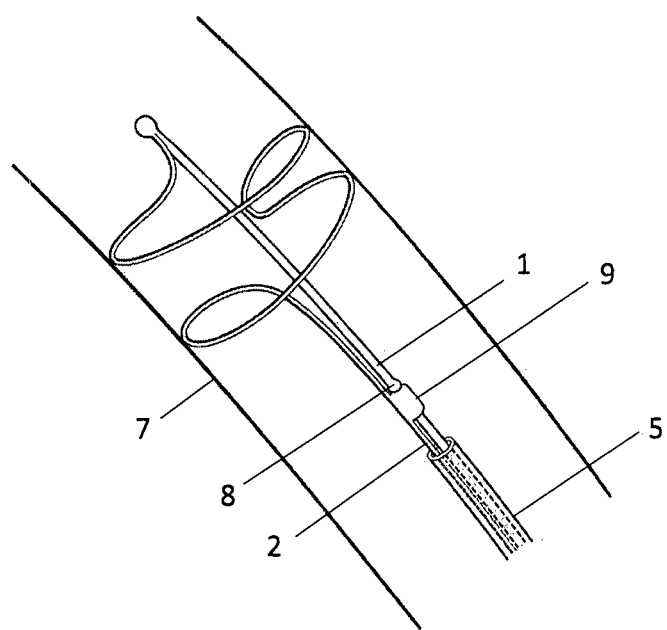
FIG. 7 depicts a precursory guiding wrapping loop.

In FIG. 7 a precursory guiding wrapping loop is shown in operation. The pulling of the spinal wire (1) is limited by means of a bulge, (8), of the spinal wire, restrained by an eyelet, (9), of the chordal wire (2). The preparatory action performed by this loop facilitates optimal alignment of the chordal wire (2) before wrapping of the thrombus is performed at a subsequent step.

Figures 8A, 8B:
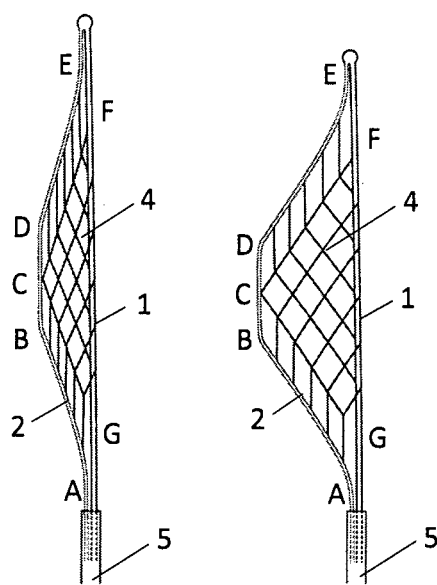
FIGS. 8A and 8B depict two phases of the trapezoidal profile configuration comprising the chordal wire, the spinal wire, and the net: semi-open, and fully open phase, respectively.

In FIG. 8A the trapezoidal profile configuration is depicted in a semi-expanded unwrapped development. The fibers of the net (4), are pre-arranged so that they form cells which obey two parallelism conditions. If C is near or at the midpoint of the chordal wire (2) then trapezium ABDE may be subdivided into one triangle, GCF, and two parallelograms, ABCG and CDEF. According to the first parallelism condition the fibers of the cells of parallelogram ABCG and of parallelogram CDEF are parallel to AE; according to the second parallelism condition the fibers of triangle GCF either coincide with CG or CF, or have one-part parallel to CG and the other parallel to CF. These conditions ensure that the net is contractible and thus collapses, practically, to a minimal structure when the chordal wire (2) is inside the catheter. Also, the net contracts, by the same design, whenever the chordal wire is pulled for extra tightening of the thrombus during the phase of narrowing the capturing cone.

In FIG. 8B the trapezoidal profile configuration is shown in fully expanded unwrapped development; the pattern of the cells of the net, (4), still complies with the parallelism conditions satisfied by its individual fibers, given that the sides of the parallelograms ABCD and CDEF maintain the same length as their counterparts in FIG. 8A.

In FIG. 9A one of many variations of the net pattern of the trapezoidal profile configuration is shown whereby parallelograms ABCG and CDEF contain more than one row of parallelogram cells each. It is possible for CDEF to contain one row of cells or no row at all, regardless of the number of rows contained in parallelogram ABCD. If parallelogram CDEF contains no row of cells, then DE and CF coincide, in which case the parallelogram vanishes altogether, collapsing to a straight-line segment, which—in the real manifestation of the design—constitutes the distal leg of the trapezoidal profile of the chordal wire (2).

In FIG. 9B one of many variations of the net pattern of the trapezoidal profile configuration is shown whereby parallelograms ABCG and CDEF contain parallelogram cells of a brick-wall type structure.

Figure 9C:
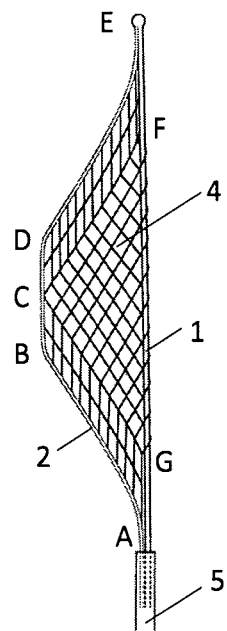
Figure 9C:
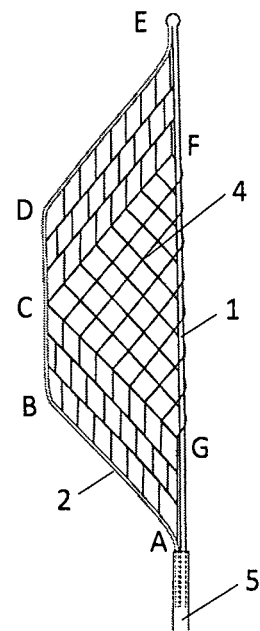
Figure 9C:
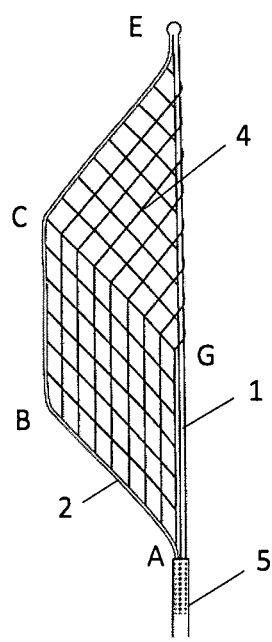

In FIG. 9C a variation of the net pattern of the trapezoidal profile configuration is illustrated in which parallelogram CDEF is taken to the limit whereby CD=FE=0, thus CF and DE coincide resulting in chordal profile ABCE. So, this configuration may be considered as the conjunction of a triangular and a parallelogram profile; additional trapezoidal formations are also possible by adjoining triangular profiles with parallelogram ones.

Figure 10:
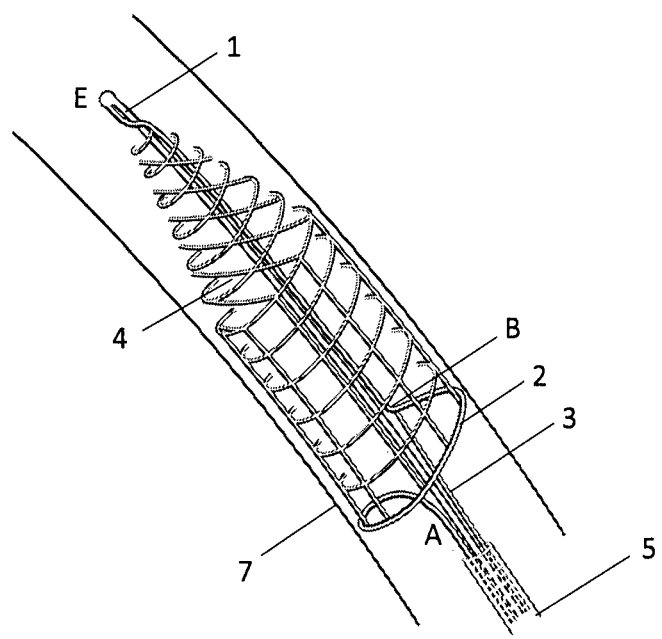
FIG. 10 depicts the reshaping of the wrapping setup of 9C into a composite conical and cylindrical configuration.

In FIG. 10 the reshaping of the wrapping setup of 9C into a composite conical and cylindrical configuration is shown; after obtaining wrapping by pulling the spinal wire (1) with respect to the chordal wire (2), string (3), which is attached at point B of the chordal wire (2), is pulled, causing alignment of the ECB portion of the chordal wire (2) with the spinal wire (1), thus imposing a conical shape to the distal portion of the wrapping net, (4), and a cylindrical shape to the posterior part of the net; subsequently, slight pulling of the chordal wire (2) will tighten the net more-so, as depicted herein.

Figure 11:
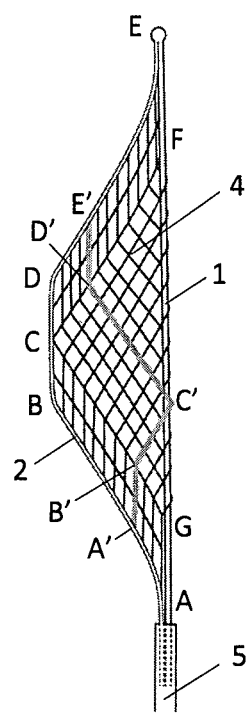
FIG. 11 depicts the fiber-length restriction that underlies its net pattern so that full contractibility is ensured.

In FIG. 11 the fiber design length-compatibility condition that underlies the net pattern—so that full contractibility is ensured—is demonstrated. If we consider the path of minimal length of any fiber attached to the chordal wire, such as A'B'C'D'E', then A'B' is parallel and equal to BC, B'C' is parallel and equal to CD', thus equal to DE', C'D' is parallel and equal to B'C thus equal to A'B, D'E' is parallel and equal to CD; then the length of the fiber A'B'C'D'E' is equal to the total length of the chordal wire segment A'BCDE', which is invariant since the ends of the fiber are permanently fixed at A' and E'. So, at all phases of development of the compound assembly comprising the spinal wire (1), the chordal wire (2), and the net, (4), each net fiber (e.g. A'B'C'D'E') complies lengthwise with the compatibility condition that its length equals the constant length of the corresponding segment of the chordal wire which is defined by the ends of the respective fiber attached onto it (e.g. A'BCDE'). If triangle GCF is not equilateral, then the fibers are not equal to each other lengthwise.

What is claimed is:

1. Wrapping cape system for removing blocking items from body vessels having a configuration comprising the interconnection of a spinal wire, a chordal wire, a net, and a pulling string, whereby the spinal wire is stiffer than the chordal wire and one end of the chordal wire is joined with an end-point of the spinal wire, forming a terminal junction, and one end of the pulling string is permanently affixed to an intermediate point of the chordal wire; all constituents are passing through a tubular guide, and are capable of sliding through the tubular guide, as well able to exit from the distal end of the tubular guide; the spinal wire, the chordal wire, and the pulling string, are having their un-joined free ends available for individual handling, directly or indirectly, through a proximal entrance of the tubular guide; the net is linking the spinal wire and the chordal wire and is contractible-expandable in accordance with the contraction condition that when the spinal wire and the chordal wire are aligned, the net is contracted in one dimension and elongated in the other, thus co-aligned with the spinal and chordal wires, whilst when the spinal and chordal wires are in a state of separation the net is expanded and undertaking a two dimensional shape; and where on deployment of the system three actions are performed, namely the wrapping action, the entrapping action, and the tightening action, associated with the performance of a sequence of handling operations involving the application of suitable relative displacements between the tubular guide, the spinal wire, the chordal wire, and the pulling string, as required accordingly, aiming to first capture and then tighten a blocking item trapped in a tubular geometry, with the aid of the accompanying net, whereby: during the wrapping stage, the spinal wire is pulled with respect to the chordal wire in the presence of the surrounding cylindrical geometry, thus imposing the cylindricality constraint upon the expanding part of the assembly, thereby curving the originating profile of the conforming netted chordal wire and forcing it to encircle the contained blocking item, thus wrapping it up to the point where the chordal wire reaches the spinal wire; next, during the entrapping stage, pulling string is pulled up until the blocking item is entrapped either by a single conical contraption, or by a conical-and-cylindrical composite formation; subsequently, during the tightening stage, further shrinkage of the net is effected via pulling of the chordal wire with respect to the spinal wire, owing to the built-in contractibility property of the net pattern; thus favorable conditions are established for ultimate removal of the blocking item via total pulling of the whole system.

2. Wrapping cape system according to claim 1, configured for replacing any individual fiber of the net, or any combination of connected segments of fibers of the net, by one or more wires.

3. Wrapping cape system according to claim 2, configured for employing a symmetrical configuration comprising two chordal wires, two pulling strings, and two linking nets, with capability of independent handling or handling in unison, for contralateral entrapping.

4. Wrapping cape system according to claim 2, further comprising an additional precursory guiding wrapping loop for optimal initial orientation of the wrapping cape system assembly with respect to the blocking item, whereby the guiding wrapping loop constitutes a physical extension of the distal end of the basic configuration, and whence the chordal wire is equipped with an eyelet, through which the spinal wire passes, and the spinal wire bears a slight bulge, so that the pulling of the spinal wire is ultimately restrained by the eyelet, of the chordal wire, thereby allowing for the implementation of a two-phase procedure where during the first phase, the tubular guide is brought sufficiently beyond the blocking item so that, when partially withdrawn, it reveals the guiding wrapping loop, which necessarily finds itself also beyond the blocking item; the spinal wire is then pulled and the wrapping action settles unimpededly the chordal wire of the guiding wrapping loop around the internal wall of the surrounding cylindrical geometry of the blocked vessel; this way the spinal and chordal wires are aligned with the confining wall and consequently they also prepare the proper orientation for the preceding portion of the main twin or triple-wire assembly; and during the second phase the procedure for wrapping the blocking item is carried out.

5. Wrapping cape system according to claim 1, wherein the softness of the spinal wire and the chordal wire is in total or in part adaptable via adapting their cross-section.

6. Wrapping cape system according to claim 1, wherein the softness of the spinal wire and the chordal wire is in total or in part adaptable via resorting to coiling through spiral winding.

7. Wrapping cape system according to claim 1, wherein the softness of the spinal wire and the chordal wire is in total or in part adaptable through thermal and/or chemical treatment of a base material, in conjunction with intentional pretension to predispose the bending of the wires during operation, accomplished through preparatory mechanical processing.

8. Wrapping cape system according to claim 1, wherein the softness of the spinal wire and the chordal wire is in total or in part adaptable through thermal and/or chemical treatment of a base material, in conjunction with intentional pretension to predispose the bending of the wires during operation, accomplished through the use of shape memory alloys.

9. Wrapping cape system according to claim 1, wherein the fibers of the net are at least sectionally parallel to the chordal wire.

10. Wrapping cape system according to claim 1, wherein each fiber of the net goes once around the spinal wire.

11. Wrapping cape system according to claim 1, wherein the length of each fiber equals the length of the corresponding segment of the chordal wire, whereby the segment is defined by the two points, where the fiber is attached to the chordal wire.

12. Wrapping cape system according to claim 1, wherein in an expanded state, the net is spanned between the spinal wire and the chordal wire in a triangular, or a trapezoidal profile or in a combination thereof.

* * * * *